United States Patent [19]

Silvestri et al.

[11] Patent Number: 5,126,147
[45] Date of Patent: Jun. 30, 1992

[54] SUSTAINED RELEASE DOSAGE FORM

[75] Inventors: Loui J. Silvestri, Miramar; H. Ruth Pyle, Ft. Lauderdale, both of Fla.

[73] Assignee: BioSearch, Inc., Plantation, Fla.

[21] Appl. No.: 476,049

[22] Filed: Feb. 8, 1990

[51] Int. Cl.$^5$ .......................... A61K 9/50; A61K 9/52; A61K 9/54; A61K 9/58
[52] U.S. Cl. ........................ 424/497; 424/422; 424/424; 424/489; 424/490; 514/885; 514/922
[58] Field of Search ............... 424/422, 424, 489, 490, 424/497; 514/922, 885

[56] References Cited

U.S. PATENT DOCUMENTS

| | | | |
|---|---|---|---|
| 3,429,827 | 2/1969 | Ruus | 424/497 |
| 3,761,585 | 9/1973 | Mullan et al. | 424/91 |
| 3,792,159 | 2/1974 | Green et al. | 424/91 |
| 3,794,630 | 2/1974 | Mullan et al. | 530/379 |
| 3,825,525 | 7/1974 | Mullan et al. | 530/379 |
| 3,893,993 | 7/1975 | Mullan et al. | 530/379 |
| 3,903,067 | 9/1975 | Mullan et al. | 530/379 |
| 3,976,071 | 8/1976 | Sadek | 424/425 |
| 3,978,203 | 8/1976 | Wise | 424/425 |
| 4,070,455 | 1/1978 | Green et al. | 424/91 |
| 4,093,709 | 6/1978 | Choi et al. | 424/424 |
| 4,131,648 | 12/1978 | Choi et al. | 424/78 |
| 4,140,679 | 2/1979 | Malley | 525/420 |
| 4,158,705 | 7/1980 | Malley | 424/91 |
| 4,164,560 | 8/1979 | Folkman et al. | 424/486 |
| 4,180,562 | 12/1979 | Patterson et al. | 424/91 |
| 4,215,036 | 7/1990 | Malley | 530/379 |
| 4,222,907 | 9/1980 | Katz | 525/54.1 |
| 4,226,853 | 10/1980 | Marsh | 424/91 |
| 4,234,569 | 11/1980 | Marsh | 424/91 |
| 4,256,732 | 3/1981 | Malley | 424/91 |
| 4,261,973 | 4/1981 | Lee et al. | 424/78 |
| 4,269,764 | 5/1981 | Patterson et al. | 530/406 |
| 4,338,297 | 7/1982 | Michael et al. | 156/345 |
| 4,351,337 | 9/1982 | Sidman | 424/425 |
| 4,428,932 | 1/1984 | Overell | 424/91 |
| 4,439,199 | 3/1984 | Amkraut et al. | 424/88 |
| 4,469,677 | 9/1984 | Michael et al. | 424/91 |
| 4,479,911 | 10/1984 | Fong | 424/497 |
| 4,526,938 | 7/1985 | Churchill et al. | 525/415 |
| 4,609,547 | 9/1986 | Garman et al. | 424/88 |
| 4,675,189 | 6/1987 | Kent et al. | 424/490 |
| 4,675,381 | 6/1987 | Bichon | 530/345 |
| 4,683,288 | 7/1987 | Tanaka et al. | 528/361 |
| 4,757,128 | 7/1988 | Domb et al. | 528/271 |
| 4,767,628 | 8/1988 | Hutchinson | 424/426 |
| 4,774,074 | 9/1988 | Snipes | 424/405 |
| 4,781,919 | 11/1988 | Liebowitz | 424/422 |
| 4,861,627 | 8/1989 | Mathiowitz et al. | 424/497 |
| 4,994,279 | 2/1991 | Aoki et al. | 424/490 |

Primary Examiner—Thurman K. Pace
Assistant Examiner—Carlos Azpuru
Attorney, Agent, or Firm—Wegner, Cantor, Mueller & Player

[57] ABSTRACT

A multiphasic sustained release injectable delivery system is provided, as well as a method for treating humans and other mammals with that multiphasic sustained release system. The multiphasic sustained release system comprises prolonged, controlled delivery of microencapsulated macromolecular bioactive agent of biological origin comprising the bioactive agent encapsulated in microcapsules of bioerodible encapsulating polymer, which permits a sustained, multiphasic release of said bioactive agent, including (i) a first portion of said bioactive agent that upon injection is capable of being released from said microcapsules of bioerodible encapsulating polymer in a manner whereby only a relatively small amount of said bioactive agent is released during said first phase, whereby initial biological reaction is minimized due to said first portion producing a mild reaction similar to that normally observed with low doses of conventional administration; and (ii) secondary portions of said bioactive agent that provide a substantially higher level of bioactive agent in doses which could provoke a serious reaction in the patient, but for the prior release of said first portion.

17 Claims, No Drawings

SUSTAINED RELEASE DOSAGE FORM

In accordance with a first aspect of the present invention there is provided a multiphasic sustained release injectable delivery system for prolonged, controlled delivery of microencapsulated macromolecular bioactive agents of biological origin. The macromolecular bioactive agents include, but are not limited to: allergen-related substances such as Allergen source material, Allergen extracts, denatured IgE or fragments thereof, Pentapeptides, and IgE receptors or fragments thereof; cytokines such as Interferon, including alpha, gamma, etc., Interleukins, including Interleukins 1, 2, 3, 4, etc., Colony Stimulating Factors including macrophage colony stimulating factors and granulocyte colony stimulating factors, Epidermal Growth Factors, Fibroblast anti-collagenase, Erythropoietin, and Tumor Necrosis Factor; Anti-Hemophilic Factor (Factor VIII), and Receptor CD4. The system comprises the bioactive agent encapsulated in microcapsules of bioerodible encapsulating polymer, which permits a sustained, multiphasic release of said bioactive agent, including (i) a first portion of bioactive agent that upon injection is capable of being released from said microcapsules of bioerodible encapsulating polymer in a manner whereby only a relatively small amount of the bioactive agent is released during a first phase, whereby the initial biological reaction to the bioactive agent is minimized due to said first portion; and (ii) secondary portions of the bioactive agent that provide substantially higher levels of the bioactive agent in doses which could provoke a serious reaction in the patient, but for the prior release of said first portion. For example, a first portion of an allergen extract will produce a mild local reaction similar to that normally observed with low doses of conventional allergen administration.

The multiphasic sustained release delivery system of the invention permits a controlled release of the bioactive agent wherein the release profile in the treated patient describes an accelerating or crescendoing dosage delivery. The term crescendoing dosage delivery is defined herein to mean the release of the bioactive agents from the polymer matrix in doses that increase progressively over time, such that the rate of delivery of the bioactive agent at the end of the therapeutic period is much greater than the rate of delivery at the beginning of the therapeutic period. The rate of delivery at the end of the therapeutic period may either continue to increase until the matrices are exhausted of the bioactive substances, or the rate of delivery may plateau for a predetermined period of time at a rate high above the initial delivery rate before the matrices are exhausted of the bioactive substances. The multiphasic sustained release delivery system of the invention may include one or more macromolecular bioactive agents of biological origin including but not limited to allergen-related substances such as Allergen source material, Allergen extracts, denatured IgE or fragments thereof, Pentapeptides, and IgE receptors or fragments thereof; cytokines such as Interferon, including alpha, gamma, etc., Interleukins including Interleukins 1, 2, 3, 4, etc., Colony Stimulating Factors including macrophage colony stimulating factors and granulocyte colony stimulating factors, Epidermal Growth Factors, Fibroblast anti-collagenase, Erythropoietin, and Tumor Necrosis Factor; Anti-Hemophilic Factor (Factor VIII), and Receptor CD4. The multiphasic sustained release delivery system may additionally include stabilizing agents including thermopreservatives such as glycerine or mannitol, adjuvant agents, and/or polymer hydrolysis modifying agents.

In a preferred embodiment, the bioactive agent is derived from naturally occurring sources. In another embodiment, the bioactive agent is genetically engineered or "cloned". In a further preferred embodiment, the bioactive agent is purified or partially purified. In a further preferred embodiment, the bioactive agent has been lyophilized. In another embodiment, stabilizing agents are used for the bioactive agent; preferred embodiments are thermopreservatives of which may be mentioned glycerine or mannitol.

The bioerodible encapsulating polymer is preferably chosen from a group of natural and synthetic polymers consisting of poly(lactides) and/or poly(glycolides) and/or copolymers and derivatives thereof; non-peptide polyamino acids; poly (ortho esters); low and high molecular weight polyanhydrides; polyiminocarbonates; poly alpha-aminoacids; polyalkyl-cyano-acrylate; polyphosphazenes; or acyloxymethyl polyaspartate and polyglutamate copolymers.

In accordance with a second aspect of the present invention there is provided a method of therapy for living organisms, particularly humans and other mammals, which comprises injecting a subject with a microencapsulated macromolecular bioactive agent of biological origin including but not limited to: allergen-related substances such as Allergen source material, Allergen extracts, denatured IgE or fragments thereof, Pentapeptides, and IgE receptors or fragments thereof; cytokines such as Interferon, including alpha, gamma, etc., Interleukins including Interleukins 1, 2, 3, 4, etc., Colony Stimulating Factors including macrophage colony stimulating factors and granulocyte colony stimulating factors, Epidermal Growth Factors, Fibroblast anti-collagenase, Erythropoietin, and Tumor Necrosis Factor; Anti-Hemophilic Factor (Factor VIII), and Receptor CD4. The bioactive agent is encapsulated in microcapsules of bioerodible encapsulating polymer, which permits a sustained, multiphasic release of said bioactive agent, including (i) a first portion of which is capable of being released in a manner whereby only a relatively small amount of the bioactive agent is released during a first phase, whereby initial adverse reactivity is minimized due to said first portion producing a mild reaction similar to that normally observed with low doses of conventional bioactive agent administration; and (ii) secondary portions of the bioactive agent that provide substantially higher levels of the bioactive agent in doses which could provoke a serious reaction in the patient, but for the prior release of said first portion.

In accordance with another aspect of the present invention, there is provided a method of allergen desensitization therapy which comprises injecting a subject with microencapsulated allergen extract. The allergen extract is encapsulated in microcapsules of bioerodible encapsulating polymer, which permits a sustained, multiphasic release of the allergen extract, including (i) a first portion of the allergen extract that upon injection is capable of being released in a manner whereby only a relatively small amount of the allergen extract is released during a first phase, whereby initial allergenicity is minimized due to said first portion producing a mild reaction similar to that normally observed with low doses of conventional allergen administration; and (ii) secondary portions of the allergen extract that provide substantially higher levels of allergen extract in doses which could provoke a serious reaction in the patient, but for the prior release of the first portion.

In accordance with yet another aspect of the present invention, there is provided a method of allergen desensitization therapy which comprises injecting a subject with microencapsulated unextracted allergen source material. The unextracted allergen source material is encapsulated in microcapsules, including (i) a first portion of said unextracted allergen source material that upon injection is capable of being exposed to body fluids and whose allergen content can thereafter be eluted in a manner whereby only a relatively small amount of allergen content is eluted during a first phase, whereby initial allergenicity is minimized due to said first portion producing a mild local reaction similar to that normally observed with low doses of conventional allergen administration; and (ii) secondary portions of unextracted allergen source material that provide substantially higher levels of allergen content in doses which could provoke a serious reaction in the patient, but for the prior release of said first portion.

The allergenic extract generally comprises one or more allergen sources including but not limited to the group of pollens, molds, foods, animal danders or their excretions, smuts and insects, their venoms or their excretions. In a preferred embodiment, the allergenic extract used is in aqueous form. The allergens also may be physically or chemically modified. In a preferred embodiment, highly allergenic, low molecular weight allergen fractions have been excluded from the chemically modified allergenic extract. In a further preferred embodiment, the allergens extracts have been lyophilized. In another embodiment, the allergenic sources are rot extracted at all, but rather are directly microencapsulated without prior extraction. In yet another embodiment, stabilizing agents are used for the allergen extract; preferred embodiments are thermopreservatives of which may be mentioned glycerine or mannitol.

In a preferred embodiment for any of the macromolecular bioactive agents, agents for symptomatic treatment of initial adverse reactions to the initial dose are included. Examples of these agents include: non-steroidal anti-inflammatory agents such as aspirin or ibuprofen; anti-histamines such as diphenhydramine, chlorpheniramine, clemastine, hydroxyzine, terfenadine promethazine, astemizole, loratadine, and the mast cell stabilizer cromolyn sodium; bronchodilators such as metaproterenol sulfate, isoetharine hydrochloride, theophylline, albuterol, and epinephrine; and corticosteroids such as prednisone, prednisolone, hydrocortisone, cortisone acetate, flunisolide, and triamincinolone acetate.

In a preferred embodiment for any of the macromolecular bioactive agents, an adjuvant is added such as tyrosine, polytyrosine, dimethylglycine (DMG), or muramyl dipeptide.

In a preferred embodiment for any of the macromolecular bioactive agents, a polymer hydrolysis modifying agent is included such as a non-toxic organic acid or base, or an acidic, neutral or basic inorganic salt, or a solution thereof.

In a preferred embodiment for any of the macromolecular bioactive agents, the variable release rate of the bioactive agent from the polymer is achieved heterogeneously by using a mixture of two or more of the following microsphere types:

1. Some types of microspheres have thinner bioactive agent-impregnated polymer layers, and others which have thicker bioactive agent-impregnated polymer layers.
2. Some types of microspheres which have higher concentrations of polymer, and others which have lower concentrations of polymer.
3. Some types of microspheres which have different ratios of copolymers which affect their rate of erosion.
4. Some types of microspheres which are made of one class of polymers, and others which are made of a different class of polymer with an intrinsically different means or rate of bioerosion.
5. Some types of microspheres which have higher concentrations of impregnated bioactive agent, and others which have lower concentrations of impregnated bioactive agent.

In a preferred embodiment, the variable release rate of the bioactive agent from the polymer is achieved homogeneously by using just one of the following types of microspheres:

1. Some types of microspheres which have thicker bioactive agent-impregnated outer polymer layers, and thinner bioactive agent impregnated polymer layers in the core.
2. Some types of microspheres in which there is a higher concentration of polymer in the outer layers of the microsphere, than in the core of the microsphere.
3. Some types of microspheres which have one ratio of copolymers in the outer layer but a different ratio of copolymer in the core of the microsphere.
4. Some types of microspheres in which the core of each microsphere is made of one class of polymers, and in which the outer layers are made of a different class of polymer with an intrinsically different means or rate of bioerosion.
5. Some types of microspheres in which the core of each microsphere contains a higher concentration of impregnated bioactive agent as compared to outer layers of each microsphere.

In a preferred embodiment, the variable release rate of the bioactive agent from the polymer is achieved through the use of a heterogeneous mixture of microspheres, some of which have hydrolysis accelerating agents impregnated in the microsphere polymer layers, while other microspheres contain hydrolysis retarding agents, or no accelerating/retarding agent at all. For example, the first portion (i) may include hydrolysis retarding agents impregnated in the microsphere polymer layers, while the microspheres corresponding to the secondary portions (ii) contain hydrolysis accelerating agents, or no accelerating agent at all. Alternatively, the first portion (i) may include hydrolysis retarding agents impregnated in the microsphere polymer layers, while the microspheres corresponding to said secondary portions (ii) contain hydrolysis accelerating agents.

EXAMPLE 1

A heterogeneous microcapsule composition is provided wherein the final product is an admixture of one lot of microcapsules containing a 50:50 ratio of the excipients poly (lactide-co-glycolide) copolymer, and the second lot of microcapsules containing a 70:30 ratio of the excipients poly(lactide-co-glycolide) copolymer. The allergen is an aqueous extract of short ragweed (Ambrosia artemisifolia) present at approximately 0.4% (w/w), and no adjuvant or polymer hydrolysis-modifying agent is present. In two separate preparations, a total of 4.0 g of the excipient (in one case at a ratio of 50:50, and in the other 70:30) is dissolved in 200 g of methylene chloride. This solution is poured into a 250 ml round bottom flask fitted with a stainless steel swivel paddle and a light-duty, variable speed stirrer. A total volume of 1.5 ml of the allergen protein in buffered saline solution containing 10 mg/ml (as measured by the ninhydrin protein assay) is added to a 5 ml vial. The contents of the round bottomed flask are stirred at 3,000 rpm while the solution containing the allergen protein is slowly added. Alternatively, the mixture could be emulsified by ultrasonics and the like, or a high pressure homogenizer.

With continued stirring, 50 ml of silicone oil is added at the rate of 5.0 ml/minute using a peristaltic pump. The addition of the silicone oil results in the separation of the polymer phase and its subsequent deposit as droplets of solvent-swollen polymer onto the surface of the water-allergen microdroplets. These solvent-swollen polymer droplets are then coalesced to form a continuous film around the water-polypeptide microdroplets.

Hardening of the microcapsules is achieved by pouring the contents of the round bottom flask into approximately 1500 ml of heptane. This mixture is stirred at approximately 1000 rpm for 30 minutes using the same stainless steel stirrer. The liquid phase (containing heptane-methylene chloride-silicone oil) is removed by using a Buchner funnel loaded with Whatman #41 or #541 filter paper. The microcapsules are repeatedly washed with 100 ml aliquots of heptane to insure complete removal of the liquid phase, especially the silicone oil. Finally, the microcapsules are washed with deionized water followed by a wash with a 1% (w/v) solution of Tween 20 and dried at room temperature in vacuo. Microcapsules prepared in this fashion have diameters ranging from 5–50 microns.

EXAMPLE 2

The procedure of Example 1 is repeated, except 50 mg/ml protein of the ragweed allergen extract is used. The resulting microspheres are then resuspended in 2.0 ml of an aqueous solution of ragweed allergen at only 10 mg protein/ml. Next, a total of 4.0 g of the excipient is dissolved in 200 g of methylene chloride, and this solution is poured into a 250 ml round bottom flask as described in Example 1. While rapidly stirring this mixture, the previously-prepared microspheres (now suspended in the aqueous solution of ragweed allergen) are slowly poured into the reaction flask. Immediately, 50 ml of silicone oil is added at the rate of 5.0 ml/minute. The product is processed as described in Example 1. The resulting product consists of microspheres containing ragweed allergen at 50 mg/ml, microspheres containing ragweed allergen at 10 mg/ml, and microspheres containing ragweed allergen with a core at 50 mg/ml and a "shell" at 10 mg ragweed protein/ml. The microspheres range in size from 5 to 400$\mu$, and are separated by mechanical sifting into various sizes. Dissolution studies demonstrate a desirable crescendoing multiphasic release profile for the larger (i.e., >100$\mu$) microspheres, thus indicating that the larger microspheres are predominantly hybrids.

EXAMPLE 3

The procedure of Example 1 is repeated, except that Timothy grass (Phleum pratense) allergen is substituted for short ragweed, diketene acetal-diol condensates (diketene acetal 3,9-bis- [methylene]-2,4,8,10-tetraoxaspiro [5,5] undecane condensed with 1,6-hexanediol) is substituted for the (lactide-co-glycolide) copolymer, and an adjuvant (glycodipeptide N-acetyl-muramyl-L-alpha-aminobutyryl-D-isoglutamine) is incorporated into the aqueous phase.

EXAMPLE 4

A total of 1.0 g of Poly(ortho ester) is dissolved in 25 ml methylene chloride. A total of 0.1 g of allergen protein from the house dust mite (Dermatophagoides farinae) is dissolved in phosphate buffered saline and 0.1% acetic acid. The microspheres are then prepared as described in Example 1.

EXAMPLE 5

Example 4 is repeated, except that the house dust mite allergen has 0.1% sodium carbonate incorporated into the aqueous solution.

EXAMPLE 6

The microspheres prepared by Example 4 ("acid" microspheres) are mixed with microspheres from Example 5 ("basic" microspheres) in a ratio of 1:1, 1:5, and 1:10 of "acid" to "base" microspheres, respectively. By preparing various mixtures of "acid" to "base" microspheres in this manner, the release profile of the product is dramatically changed. Specifically, the 1:1 mixture results in a slow initial release, and only a slightly elevated secondary release, whereas the 1:10 mixture results in an intermediate initial release, and a highly elevated secondary release.

EXAMPLE 7

The procedure of Example 1 is repeated in substantial measure, except that a glutaraldehyde-modified ragweed allergen extract is used.

EXAMPLE 8

The procedure of Example 1 is repeated, except an alum-adsorbed ragweed allergen extract is used.

EXAMPLE 9

The procedure of Example 1 is followed, except microspheres are prepared with 5–60% glycerol incorporated into the aqueous phase as a thermopreservative for the ragweed allergen extract.

EXAMPLE 10

This experiment is essentially the same as Example 1, except ragweed pollen instead of an aqueous ragweed extract is incorporated into the microspheres.

EXAMPLE 11

This experiment is essentially the same as Example 1, except that lyophilized ragweed extract particles is first mechanically ground and sieved to produce a powder of approximately 10$\mu$ or smaller in size. The organic solvent is then loaded with these lyophilized allergen particles which is dispersed throughout the solution by stirring. Additional processing continues essentially as described in Example 1.

EXAMPLE 12

This experiment is essentially the same as Example 2, except the reencapsulation is performed with an aqueous solution devoid of allergen. The final product consists of small microspheres without encapsulated allergen, small microspheres with the original concentration of allergen, and large microspheres that have an allergen core, but a thick encapsulating wall. These latter microspheres are appropriate in admixtures with thin-walled microsphere to produce the desired multi-linear release profile.

EXAMPLE 13

A heterogeneous microcapsule composition is provided wherein the final product is an admixture of one lot of microcapsules containing a 50:50 ratio of the excipients poly(lactide-co-glycolide) copolymer, and the second lot of microcapsules containing a 70:30 ratio of the excipients poly(lactide-co-glycolide) copolymer. The bioactive agent is an aqueous solution of leukocyte-derived alpha interferon present at approximately 0.4% (w/w), and no adjuvant or polymer hydrolysis-modifying agent is present. In two separate preparations, a total of 4.0 g of the excipient (in one case at a ratio of 50:50, and in the other 70:30) is dissolved in 200 g of methylene chloride. This solution is poured into a 250 ml round bottom flask fitted with a stainless steel swivel paddle and a light-duty, variable speed stirrer. A total volume of 1.5 ml of the interferon protein in buffered saline solution containing 10 million units is added to the 5 ml vial. The contents of the round bottomed flask are stirred at 3,000 rpm while a solution containing the interferon protein is slowly added. Alternatively, the mixture could be emulsified by ultrasonics and the like, or a high pressure homogenizer.

With continued stirring, 50 ml of silicone oil is added at the rate of 5.0 ml/minute using a peristaltic pump. The addition of the silicone oil results in the separation of the polymer phase and its subsequent deposit as droplets of solvent-swollen polymer onto the surface of the water-allergen microdroplets. These solvent-swollen droplets are then coalesced to form a continuous film around the water-polypeptide microdroplets.

Hardening of the microcapsules is achieved by pouring the contents of the round bottom flask into approximately 1500 ml of heptane. This mixture is stirred at approximately 1000 rpm for 30 minutes using the same stainless steel stirrer. The liquid phase (containing heptane-methylene chloride-silicone oil) is removed by using a Buchner funnel loaded with Whatman #41 or #541 filter paper. The microcapsules are repeatedly washed with 100 ml aliquots of heptane to insure complete removal of the liquid phase, especially the silicone oil. Finally, the microcapsules are washed with deionized water followed by a wash with a 1% (w/v) solution of Tween 20 and dried at room temperature in vacuo. Microcapsules prepared in this fashion have diameters ranging from 5–50 microns.

EXAMPLE 14

The procedure of Example 13 is repeated, except 100 million units of leukocyte-derived alpha interferon protein is used. The resulting microspheres are then resuspended in 2.0 ml of an aqueous solution of interferon protein at only 10 million units of interferon/ml. Next, a total of 4.0 g of the excipient is dissolved in 200 g of methylene chloride, and this solution is poured into a 250 ml round bottom flask as described in Example 13. While rapidly stirring this mixture, the previously-prepared microspheres (now suspended in the aqueous solution of interferon protein) are slowly poured into the reaction flask. Immediately, 50 ml of silicone oil is added at the rate of 5.0 ml/minute. The product is processed as described in Example 13. The resulting product consists of microspheres containing interferon at 100 million units/ml, microspheres containing interferon at 10 million units/ml, microspheres containing interferon with a core at 100 million units/ml, and a "shell" containing interferon at 10 million units/ml. The microspheres range in size from 5 to 400$\mu$, and are separated by mechanical sifting into various sizes. Dissolution studies demonstrate a desirable crescendoing multiphasic release profile for the larger (i.e., $>100\mu$) microspheres, thus indicating that the larger microspheres are predominantly hybrids.

What is claimed is:

1. A multiphasic sustained release delivery system for prolonged, controlled delivery of microencapsulated macromolecular bioactive agent, comprising a macromolecular bioactive agent of a biological origin encapsulated in microcapsules of bioerodible encapsulating polymer, which permits a sustained, multiphasic release of said macromolecular bioactive agent, including:

(i) a first portion of said macromolecular bioactive agent that upon injection is capable of being released from said microcapsules of bioerodible encapsulating polymer in a manner whereby only a relatively small amount of said macromolecular bioactive agent is released during a first phase, whereby initial biological reaction is minimized due to said first portion producing a mild local reaction similar to that normally observed with low doses of conventional administration; and (ii) a second portion of said macromolecular bioactive agent for release from said microcapsules after said initial biological reaction is minimized by said first portion to provide a substantially higher level of the macromolecular bioactive agent in doses which could provoke a serious reaction in the patient, but for the prior release of said first portion.

2. A multiphasic sustained release delivery system according to claim 1 wherein the macromolecular bioactive agent is selected from the group consisting of allergen-related substances, cytokines, anti-hemophilic factors and Receptor CD4.

3. A multiphasic sustained release delivery system according to claim 1 wherein the first and second portions of said macromolecular bioactive agent provide a controlled release providing a dosage profile having an accelerating or crescendoing release.

4. A multiphasic sustained release injectable delivery system for prolonged, controlled delivery of microencapsulated macromolecular bioactive agent in accordance with claim 1, wherein the harmful effects of the released macromolecular bioactive agents are controlled by the synchronous release of an agent for symptomatic treatment of initial adverse reactions to the initial dose.

5. A multiphasic sustained release injectable delivery system of claim 4 wherein said agent for symptomatic treatment comprises a non-steroidal anti-inflammatory agent, an anti-histamine, a corticosteroid, or a bronchodilator.

6. A multiphasic sustained release injectable delivery system for prolonged, controlled delivery of microencapsulated macromolecular bioactive agent of claim 1, wherein said bioerodible encapsulating polymer is a member selected from the group of poly(lactides), poly(glycolides), and copolymers and derivatives thereof; non-peptide polyamino acids; poly (ortho esters); low and high molecular weight polyanhydrides; polyiminocarbonates; poly alpha-aminoacids; polyalkyl-cyano-acrylate; polyphosphazenes; and acyloxymethyl polyaspartate and polyglutamate copolymers.

7. A multiphasic sustained release injectable delivery system for prolonged, controlled delivery of microencapsulated bioactive agent of claim 1, wherein the multiphasic release rate is achieved by providing a mixture of microspheres, those corresponding to said first portion (i) including hydrolysis retarding agents impregnated in the microsphere polymer layers, while the microspheres corresponding to said second portion (ii) either contain hydrolysis accelerating agents, or no accelerating agent at all.

8. A multiphasic sustained release injectable delivery system of claim 7 wherein said hydrolysis retarding and accelerating agents are non-toxic organic acids or bases, or an acidic, neutral or basic inorganic salt, or a solution thereof.

9. A multiphasic sustained release injectable delivery system for prolonged, controlled delivery of microencapsulated bioactive agent of claim 1, wherein the multiphasic release rate is achieved by providing a mixture of microspheres, those corresponding to said first portion (i) may include no hydrolysis retarding agents impregnated in the microsphere polymer layers, while the microspheres corresponding to said second portion (ii) contain hydrolysis accelerating agents.

10. A multiphasic sustained release injectable delivery system of claim 9 wherein said hydrolysis retarding and accelerating agents are non-toxic organic acids or bases, or an acidic, neutral or basic inorganic salt, or a solution thereof.

11. A multiphasic sustained release injectable delivery system of claim 1 wherein a stabilizing agent is encapsulated along with the bioactive agent.

12. A multiphasic sustained release injectable delivery system of claim 11 wherein said stabilizing agent is the thermopreservative glycerine or mannitol.

13. A multiphasic sustained release injectable delivery system of claim 1 wherein an adjuvant is encapsulated along with the bioactive agent.

14. A multiphasic sustained release injectable delivery system of claim 13 wherein said adjuvant is tyrosine, polytyrosine, dimethylglycine (DMG), or muramyl dipeptide.

15. A multiphasic sustained release injectable delivery system of claim 1 wherein the encapsulated bioactive agent is in aqueous form.

16. A multiphasic sustained release injectable delivery system of claim 1 wherein the encapsulated bioactive agent is in lyophilized form.

17. A multiphasic sustained release injectable delivery system of claim 1 wherein the macromolecular bioactive agent is unextracted allergen source material.

* * * * *